United States Patent
Hodges et al.

(10) Patent No.: US 9,896,717 B2
(45) Date of Patent: Feb. 20, 2018

(54) MAGNETIC IMMUNO DIGITAL PCR ASSAY

(71) Applicant: Bio-Rad Laboratories, Inc., Hercules, CA (US)

(72) Inventors: Shawn Hodges, Newark, CA (US); Nick Heredia, Mountain House, CA (US); Jonathan Petersen, Redwood City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 900 days.

(21) Appl. No.: 14/272,370

(22) Filed: May 7, 2014

(65) Prior Publication Data

US 2014/0336068 A1  Nov. 13, 2014

Related U.S. Application Data

(60) Provisional application No. 61/821,530, filed on May 9, 2013, provisional application No. 61/837,533, filed on Jun. 20, 2013.

(51) Int. Cl.
*G01N 33/53* (2006.01)
*C12Q 1/68* (2018.01)

(52) U.S. Cl.
CPC .................................. *C12Q 1/6804* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,863,736 | A | 1/1999 | Haaland |
| 8,831,887 | B2 | 9/2014 | Gorfinkel et al. |
| 8,940,882 | B2 | 1/2015 | Collis |
| 2007/0274515 | A1 | 11/2007 | McNutt et al. |
| 2008/0014589 | A1 | 1/2008 | Link et al. |
| 2010/0173394 | A1 | 7/2010 | Colston, Jr. et al. |
| 2010/0203538 | A1 | 8/2010 | Dube et al. |
| 2011/0092373 | A1 | 4/2011 | Colston, Jr. et al. |
| 2011/0092376 | A1 | 4/2011 | Colston, Jr. et al. |
| 2012/0045748 | A1 | 2/2012 | Willson et al. |
| 2012/0122714 | A1 | 5/2012 | Samuels et al. |
| 2013/0252262 | A1 | 9/2013 | Srinivasan et al. |
| 2014/0178889 | A1 | 6/2014 | Do et al. |
| 2014/0228239 | A1 | 8/2014 | McCoy et al. |

FOREIGN PATENT DOCUMENTS

| | | |
|---|---|---|
| EP | 1615948 A2 | 1/2006 |
| WO | 2004/083902 A2 | 9/2004 |
| WO | 2010/036352 A1 | 4/2010 |
| WO | 2012/129187 A1 | 9/2012 |
| WO | 2013/019751 A1 | 2/2013 |

OTHER PUBLICATIONS

O'Kennedy et al. (Biochem Education 1990 vol. 18, p. 136-140).*
Extended European Search Report from EP Appln. No. 14794346.8, dated Jan. 10, 2017.
Gibson et al., "A novel method for real time quantitative RT-PCR", *Genome Research*, vol. 6, No. 10, pp. 995-1001 (1996).
Heid et al., "Real Time Quantitative PCR", *Genome Research*, vol. 6, pp. 986-994 (1996).
Holland et al., "Detection of specific polymerase chain reaction product by utilizing the 5'—3' exonuclease activity of Thermus aquaticus DNA polymerase", *Proc. Natl. Acad. Sci. USA*, vol. 4, No. 88, pp. 7276-7280 (1991).
Livak et al., "Oligonucleotides with Fluorescent Dyes at Opposite Ends Provide a Quenched Probe System Useful for Detecting PCR Product and Nucleic Acid Hybridization", *PCR Methods and Applications*, vol. 4, pp. 357-362 (1995).
Tyagi et al., "Molecular beacons: probes that fluoresce upon hybridization", *Nature Biotechnology*, vol. 14, pp. 303-308 (1996).
Tyagi et al., "Multicolor molecular beacons for allele discrimination", *Nat. Biotechnol.*, vol. 16, pp. 49-53 (1998).
McDermott et al., "Multiplexed target detection using DNA-binding dye chemistry in droplet digital PCR", *Anal. Chem.*, vol. 85, No. 23, pp. 11619-11627 (2013).
International Search Report and Written Opinion dated Sep. 26, 2014 issued for PCT Patent Application No. PCT/US2014/037181, 14 pages.

* cited by examiner

*Primary Examiner* — Changhwa J Cheu
(74) *Attorney, Agent, or Firm* — Kilpatrick Townsend & Stockton LLP

(57) ABSTRACT

The present invention provides methods of detecting an antigen in a sample comprising contacting the sample with affinity agents to form an antigen-affinity agent-label complex, separating the antigen-affinity agent-label complex from uncomplexed components, partitioning label from the separated sample into multiple partitions, and detecting the presence of the label in one or more partitions. Compositions and kits for detecting an antigen in a sample are also provided.

17 Claims, 7 Drawing Sheets

Scheme 2, ELISA-Like Variant

Scheme 4, Detecting Antibody Analyte

MAGNETIC IMMUNO DIGITAL PCR ASSAY

CROSS-REFERENCE TO RELATED APPLICATIONS

The present application claims priority to U.S. Provisional Application No. 61/821,530, filed May 9, 2013, and to U.S. Provisional Application No. 61/837,533, filed Jun. 20, 2013, each of which is incorporated by reference herein for all purposes.

BACKGROUND OF THE INVENTION

The quantification of antigens in a sample can provide useful information for a number of clinical applications. One method for detecting and quantifying antigens is by enzyme-linked immunosorbent assay (ELISA). However, the limits of detection and precision of quantification that can be achieved with this assay are not sufficient for many applications.

Thus, there remains a need for methods of detecting and quantifying antigens that offer improved precision of quantification and low end sensitivity.

BRIEF SUMMARY OF THE INVENTION

In one aspect, methods of detecting an antigen in a sample are provided. In some embodiments, the method comprises:
  contacting the sample with a first affinity agent and a second affinity agent, wherein the second affinity agent is linked to a magnetic bead and wherein the first and second affinity agents specifically bind to the antigen, if present;
  contacting the sample comprising the first and second affinity agents with a third affinity agent, wherein the third affinity agent comprises a label and wherein the third affinity agent specifically binds to the first affinity agent, thereby forming an antigen-affinity agent-label complex;
  separating the antigen-affinity agent-label complex from uncomplexed components in the sample comprising the antigen-affinity agent-label complex based on the presence or absence of the magnetic bead, thereby generating a separated sample comprising the antigen-affinity agent-label complex;
  partitioning at least the label from the separated sample into a plurality of partitions; and
  detecting the presence of the label in at least one partition; thereby detecting the presence of the antigen.

In some embodiments, the method comprises:
  contacting the sample with a first affinity agent and a second affinity agent, wherein the first affinity agent comprises a label, wherein the second affinity agent is linked to a magnetic bead, and wherein the first and second affinity agents specifically bind to the antigen, if present, thereby forming an antigen-affinity agent-label complex;
  separating the antigen-affinity agent-label complex from uncomplexed components in the sample comprising the antigen-affinity agent-label complex based on the presence or absence of the magnetic bead, thereby generating a separated sample comprising the antigen-affinity agent-label complex;
  partitioning at least the label from the separated sample into a plurality of partitions; and
  detecting the presence of the label in at least one partition; thereby detecting the presence of the antigen.

In some embodiments, the label that is partitioned is in the antigen-affinity agent-label complex. In some embodiments, the label is cleaved from the antigen-affinity agent-label complex prior to the partitioning step.

In some embodiments, after the separating step and before the partitioning step, the method further comprises resuspending at least the label from the separated sample in a solution.

In another aspect, methods of detecting an antibody analyte in a sample, wherein the antibody analyte specifically binds to a particular antigen, are provided. In some embodiments, the method comprises:
  contacting the sample with the antigen and a first affinity agent, wherein the first affinity agent is linked to a magnetic bead and specifically binds to the antigen, thereby forming an analyte-antigen-affinity agent complex;
  contacting the sample comprising the analyte-antigen-affinity agent complex with a second affinity agent, wherein the second affinity agent comprises a label and specifically binds to the antibody analyte, thereby forming an analyte-antigen-affinity agent-label complex;
  separating the analyte-antigen-affinity agent-label complex from uncomplexed components in the sample based on the presence or absence of the magnetic bead, thereby generating a separated sample comprising the analyte-antigen-affinity agent-label complex;
  partitioning at least the label from the separated sample into a plurality of partitions; and
  detecting the presence of the label in at least one partition; thereby detecting the presence of the antibody analyte.

In some embodiments, the label that is partitioned is in the analyte-antigen-affinity agent-label complex. In some embodiments, the label is cleaved from the analyte-antigen-affinity agent-label complex prior to the partitioning step.

In some embodiments, each of the first, second, and/or third affinity agents is selected from the group consisting of antibodies, aptamers, and non-antibody protein scaffolds. In some embodiments, each of the first, second, and/or third affinity agents is an antibody.

In some embodiments, the label is a nucleic acid label. In some embodiments, the nucleic acid label comprises a detectable tag. In some embodiments, the detectable tag is a fluorophore. In some embodiments, the detectable tag is an intercalating dye.

In some embodiments, the nucleic acid label is amplified prior to the detecting step. In some embodiments, the nucleic acid label is amplified in the presence of a probe comprising a fluorophore and a quencher, wherein amplification of the nucleic acid label generates a fluorescent signal from the probe. In some embodiments, the solution comprises reagents for nucleic acid amplification. In some embodiments, the nucleic acid label is not amplified before the detection step.

In some embodiments, the label is an enzyme, and the detecting comprises detecting a product generated by the enzyme. In some embodiments, the enzyme is selected from the group consisting of horseradish peroxidase, β-galactosidase, luciferase, alkaline phosphatase, an esterase that hydrolyzes fluorescein diacetate, and a polymerase. In some embodiments, the enzyme is a DNA polymerase, and the detecting comprises detecting a nucleic acid amplification product generated by the DNA polymerase.

In some embodiments, the label is a fluorophore. In some embodiments, the detecting comprises detecting the signal generated by the fluorophore label.

In some embodiments, the label is covalently bound to the first, second, and/or third affinity agents at least prior to forming the antigen-affinity agent-label complex or analyte-antigen-affinity agent-label complex (e.g., when the first, second, and/or third affinity agents are contacted to the sample).

In some embodiments, the antigen-affinity agent-label complex is separated from uncomplexed components in the sample comprising the antigen-affinity agent-label complex, or the analyte-antigen-affinity agent-label complex is separated from uncomplexed components in the sample comprising the analyte-antigen-affinity agent-label complex, using a magnet that attracts the magnetic bead linked to an affinity agent in the antigen-affinity agent-label complex (e.g., a magnetic bead linked to an affinity agent in an antigen-affinity agent-label complex or an analyte-antigen-affinity agent-label complex).

In some embodiments, the label from the separated sample (e.g., a label in an antigen-affinity agent-label complex or analyte-antigen-affinity agent-label complex, or label that has been cleaved from an antigen-affinity agent-label complex or analyte-antigen-affinity agent-label complex) is partitioned into a sufficient number of partitions such that, on average, at least one partition lacks a copy of the label.

In some embodiments, the partitions are droplets. In some embodiments, the droplets are surrounded by an immiscible carrier fluid.

In some embodiments, the first affinity agent and the second affinity agent specifically bind to the antigen with about equal affinities. In some embodiments, the first affinity agent and the second affinity agent specifically bind to the antigen with different affinities.

In some embodiments, the antigen is a protein, an immunogen, a polysaccharide, a toxin, a cell wall, a cell capsule, a viral capsule, a viral coat, a flagellum, a fimbria or pilus, a microorganism, a nucleic acid complexed to a protein or a polysaccharide, or a lipid complexed to a protein or a polysaccharide.

In some embodiments, the method comprises detecting the label, thereby qualifying the presence of antigen or antibody analyte.

In some embodiments, the method further comprises quantifying the number of partitions comprising the label, thereby quantifying the amount of antigen or antibody analyte.

In some embodiments, the method further comprises detecting two or more distinct antigens or two or more distinct antibody analytes in the sample.

In another aspect, partition libraries for detecting an antigen or an antibody analyte in a sample are provided. In some embodiments, the partition library comprises two or more partitions as described herein, wherein at least some of the partitions comprise a first affinity agent and a second affinity agent; wherein the first affinity agent comprises a label; wherein the second affinity agent is linked to a magnetic bead; and wherein each of the first and second affinity agents specifically binds to the antigen, if present. In some embodiments, the partition library comprises two or more partitions as described herein, wherein at least some of the partitions comprise a first affinity agent, a second affinity agent, and a third affinity agent; wherein each of the first and second affinity agents specifically binds to an antigen, if present; wherein the second affinity agent is linked to a magnetic bead; and wherein the third affinity agent comprises a label and specifically binds to the first affinity agent. In some embodiments, the partition library comprises two or more partitions, wherein at least some of the partitions comprise an antigen to which the antibody analyte specifically binds, a first affinity agent, and a second affinity agent; wherein the first affinity agent is linked to a magnetic bead and specifically binds to the antigen; and wherein the second affinity agent comprises a label and specifically binds to the antibody analyte, if present.

In some embodiments, the label is a nucleic acid label. In some embodiments, the nucleic acid label comprises a detectable tag. In some embodiments, the label is an enzyme. In some embodiments, the enzyme is horseradish peroxidase, β-galactosidase, luciferase, alkaline phosphatase, an esterase that hydrolyzes fluorescein diacetate, or a polymerase.

In some embodiments, the partition library comprises at least 500 partitions. In some embodiments, at least some partitions comprise a label. In some embodiments, the partition library comprises a sufficient number of partitions such that, on average, at least one partition lacks a copy of the label.

In some embodiments, the partitions are droplets. In some embodiments, the droplets are surrounded by an immiscible carrier fluid.

In still another aspect, kits for detecting an antigen or an antibody analyte in a sample are provided. In some embodiments, the kit comprises one or more affinity agents as described herein. In some embodiments, the one or more affinity agents are selected from the group consisting of antibodies, aptamers, and non-antibody protein scaffolds. In some embodiments, the affinity agent is an antibody.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "antigen" refers to a substance that is capable of evoking the production of an antibody. Exemplary antigens include, but are not limited to, a protein, an immunogen, a polysaccharide, a toxin, a cell wall, a cell capsule, a viral capsule, a viral coat, a flagellum, a fimbria or pilus, a microorganism, a nucleic acid complexed to a protein or a polysaccharide, or a lipid complexed to a protein or a polysaccharide.

The term "affinity agent" refers to a molecule that specifically binds to an antigen. Exemplary affinity agents include, but are not limited to, an antibody, an antibody fragment, a non-antibody protein scaffold, an antibody mimetic, or an aptamer. In some embodiments, the affinity agent is an antibody.

The term "antibody analyte" refers to an antibody or antibody fragment that specifically binds to a particular antigen.

The term "binds," as used with respect to an affinity agent or an antibody analyte binding to an antigen, typically indicates that the affinity agent (e.g., an antibody) or antibody analyte, respectively, binds a majority of the antigen in a pure population, assuming an appropriate molar ratio of affinity agent or antibody analyte to antigen. For example, an affinity agent that binds a given antigen typically binds to at least ⅔ of the antigen molecules in a solution (e.g., 75%, 80%, 85%, 90%, 91%, 92%, 93%, 94%, 95%, 96%, 97%, 98%, 99%, or 100%). One of skill will recognize that some variability will arise depending on the method and/or threshold of determining binding.

The term "specifically binds to," as used with reference to an affinity agent or an antibody analyte, refers to an affinity agent (e.g., an antibody) or antibody analyte, respectively, that binds to an antigen with at least 2-fold greater affinity than to non-antigen molecules, e.g., at least 4-fold, 5-fold, 6-fold, 7-fold, 8-fold, 9-fold, 10-fold, 20-fold, 25-fold, 50-fold, or 100-fold greater affinity. For example, an affinity agent that specifically binds a particular antigen will typically bind the antigen with at least a 2-fold greater affinity than to a non-antigen molecule.

The terms "label" and "detectable label" interchangeably refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, enzymes, biotin, digoxigenin, or haptens and proteins, nucleic acids, or other entities which may be made detectable, e.g, by incorporating a radiolabel into an oligonucleotide, peptide, or antibody specifically reactive with a target molecule. Any method known in the art for conjugating an antibody to the label may be employed, e.g., using methods described in Hermanson, *Bioconjugate Techniques* 1996, Academic Press, Inc., San Diego.

The term "linked," for example as used with reference to an affinity agent linked to a magnetic bead, refers to being bound, either covalently, through a linker or a chemical bond, or noncovalently, through ionic, van der Waals, electrostatic, or hydrogen bonds.

The term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

DETAILED DESCRIPTION OF THE INVENTION

I. Introduction

Figure 1:
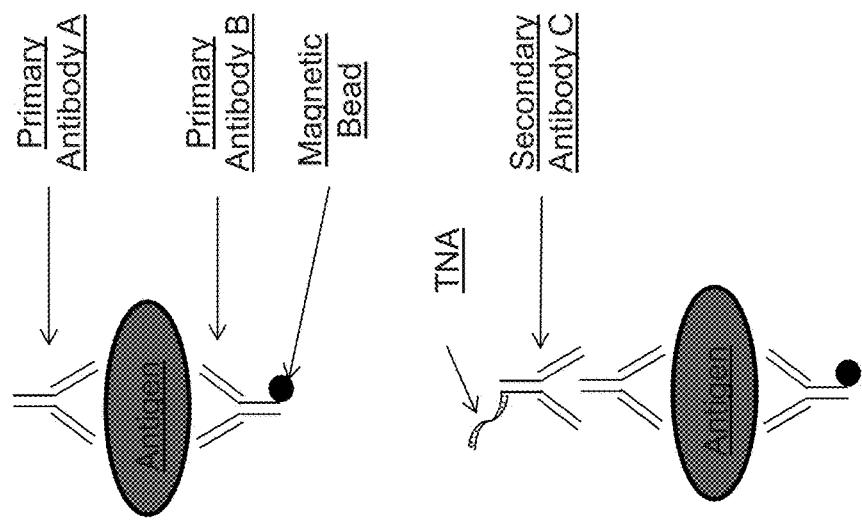
FIG. 1. Overview of "Scheme 1" for detecting an antigen. According to this scheme, an antigen binds specifically to two affinity agents (primary antibodies), A and B. Antibody B has a magnetic bead covalently attached. "Sandwich" detection is performed via a secondary antibody C that is labeled with a tagged nucleic acid ("TNA"). Free primary antibody A and secondary antibody C are washed by magnetic separation, then the antigen-primary antibody-secondary antibody-TNA complex is captured in droplets. The TNA label is amplified by droplet digital PCR ("ddPCR") and the antigen is detected.

The present invention provides methods, compositions, and kits for detecting one or more antigens or antibody analytes in a sample. Samples are contacted with labeled affinity agents (such as antibodies) that specifically bind to an antigen that may be present in the sample. The samples are then partitioned into a number of partitions and analyzed for the presence of label (e.g., in a complex with antigen and affinity agent), e.g., using digital analysis. In some embodiments, a label to be detected is amplified prior to detection, such as a nucleic acid label that can be amplified, e.g., using droplet digital PCR. The methods described herein allow for improved sensitivity of detecting an antigen or antibody analyte in a sample and/or precise quantification of antigen or antibody analyte in a sample.

II. Methods of Detecting an Antigen

In one aspect, methods of detecting an antigen of interest in a sample using an affinity agent that specifically binds to the antigen are provided. In some embodiments, the method comprises:
  contacting the sample with a first affinity agent, wherein the first affinity agent comprises a label and specifically binds to the antigen, if present, thereby forming an antigen-affinity agent-label complex;
  contacting the sample comprising the antigen-affinity agent-label complex with a second affinity agent, wherein the second affinity agent is linked to a magnetic bead and specifically binds to the first affinity agent that is not bound in the antigen-affinity agent-label complex;
  separating the antigen-affinity agent-label complex from uncomplexed components in the sample based on the presence or absence of the magnetic bead, thereby generating a separated sample comprising the antigen-affinity agent-label complex;
  partitioning at least the label from the separated sample into a plurality of partitions; and
  detecting the presence of the label in at least one partition; thereby detecting the presence of the antigen.
In some embodiments, the method comprises:
  contacting the sample with a first affinity agent and a second affinity agent, wherein the first affinity agent comprises a label, wherein the second affinity agent is linked to a magnetic bead, and wherein the first and second affinity agents specifically bind to the antigen, if present, thereby forming an antigen-affinity agent-label complex;
  separating the antigen-affinity agent-label complex from uncomplexed components in the sample comprising the antigen-affinity agent-label complex based on the presence or absence of the magnetic bead, thereby generating a separated sample comprising the antigen-affinity agent-label complex;
  partitioning at least the label from the separated sample into a plurality of partitions; and
  detecting the presence of the label in at least one partition; thereby detecting the presence of the antigen.
In some embodiments, the label that is partitioned is in the antigen-affinity agent-label complex. In some embodiments, the label is cleaved from the antigen-affinity agent-label complex prior to the partitioning step.

The methods described herein can be used to detect one or more antigens in any type of sample. In some embodiments, the sample is a biological sample. Biological samples can be obtained from any biological organism, e.g., an animal, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc.

In some embodiments, the one or more antigens to be detected are peptides, proteins (e.g., antibodies, enzymes, growth regulators, clotting factors, or phosphoproteins), immunogens, polysaccharides, toxins, cell walls, cell capsules, viral capsules, viral coats, flagellae, fimbriae or pili, microorganisms, nucleic acids complexed to protein or polysaccharide, or lipids complexed to protein or polysaccharide. In some embodiments, the antigen is a protein.

In some embodiments, two, three, four, five, or more different antigens are to be detected. In some embodiments, wherein two or more different antigens are to be detected, the two or more different antigens are the same type of antigen (e.g., two or more proteins present in a complex). In some embodiments, wherein two or more different antigens are to be detected, the two or more different antigens are different types of antigens.

Affinity Agents

An affinity agent suitable for use according to the methods described herein is any molecule that specifically binds to an antigen of interest. Non-limiting examples of affinity agents include an antibody, an antibody fragment, a non-antibody protein scaffold, an antibody mimetic, or an aptamer.

In some embodiments, the affinity agent is an antibody. As used herein, "antibody" refers to a polypeptide of the immunoglobulin family or a polypeptide comprising fragments of an immunoglobulin that is capable of noncovalently, reversibly, and in a specific manner binding a corresponding antigen. The term antibody also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). Methods for the preparation of antibodies are known in the art; see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985).

In some embodiments, the affinity agent is an antibody mimetic. An "antibody mimetic," as used herein, refers to a molecule (e.g., a peptide, protein, nucleic acid, or small molecule) that exhibits antigen binding similar to an antibody but which is not structurally related to the antibody. In some embodiments, the antibody mimetic is an artificial molecule.

In some embodiments, the affinity agent is a non-antibody protein scaffold. As used herein, a "non-antibody protein scaffold" refers to a non-immunogenic polypeptide that is capable of binding to an antigen with high specificity. In some embodiments, the protein scaffold has a structure derived from protein A, a lipocalin, a fibronectin domain, an ankyrin consensus repeat domain, or thioredoxin. Methods of preparing non-antibody scaffolds are known in the art; see, e.g., Binz and Pluckthun, *Curr Opin Biotechnol* 16:459-469 (2005); Koide et al., *J Mol Biol* 415:393-405 (2012); and Gilbreth and Koide, *Curr Opin Struct Biol* 22:413-420 (2012).

In some embodiments, the affinity agent is an aptamer. An "aptamer," as used herein, refers to a DNA or RNA molecule that has a specific binding affinity for an antigen, such as a protein or nucleic acid. In some embodiments, aptamers are selected from random pools based on their ability to bind other molecules with high affinity specificity based on non-Watson and Crick interactions with a target molecule (e.g., an antigen of interest) (see, e.g., Cox and Ellington, *Bioorg. Med. Chem.* 9:2525-2531 (2001); Lee et al., *Nuc. Acids Res.* 32:D95-D100 (2004)). For example, aptamers can be selected using a selection process known as Systematic Evolution of Ligands by Exponential Enrichment (SELEX). See, e.g., Gold et al., U.S. Pat. No. 5,270,163. Aptamers can be selected which bind, for example, nucleic acids, proteins, small organic compounds, vitamins, or inorganic compounds.

Magnetic Beads

In some embodiments, complexed antigen-affinity agent-label in the sample is separated from uncomplexed components (e.g., uncomplexed affinity agent(s) and uncomplexed antigen, if present, in the sample) based on the presence or absence of a magnetic bead that is linked to an affinity agent. A magnetic bead suitable for linking to an affinity agent as described herein can comprise any paramagnetic, superparamagnetic, or ferromagnetic material and may comprise any shape. For example, a magnetic bead can be shaped substantially like a sphere, cube, tetrahedron, octahedron, dodecahedron, icosahedron, etc. In some embodiments, combinations of two or more shapes of magnetic beads can be used for linking to an affinity agent. In some embodiments, the magnetic beads are substantially uniform in size, shape, and/or surface area.

Magnetic beads can be linked to affinity agents in a variety of ways, such as by the formation of covalent bonds, ionic bonds, hydrogen bonding, or by Van der Waals interactions. In some embodiments, the magnetic bead is linked to an affinity agent via a covalent bond. Covalent bonds can be formed by a variety of reactions, such as transamidation. In some embodiments, the magnetic bead is linked to an affinity agent via a cross-linker. In some embodiments, the cross-linker is a member selected from the group consisting of a heterobifunctional crosslinker and a homobifunctional crosslinker. In some embodiments, the cross-linker is a homobifunctional crosslinker. In some embodiments, the cross-linker is bis(sulfosuccinimidyl)suberate (BS3), ethylene glycol bis[succinimidylsuccinate] (EGS), ethylene glycol bis[sulfosuccinimidylsuccinate] (sulfo-EGS), bis[2-(succinimidooxycarbonyloxy)ethyl]sulfone (BSOCOES), dithiobis(succinimidyl)propionate (DSP), 3,3'-dithiobis(sulfosuccinimidylpropionate) (DTSSP), disuccinimidyl suberate (DSS), disuccinimidyl glutarate (DSG), methyl N-succinimidyl adipate (MSA), disuccinimidyl tartarate (DST), 1,5-difluoro-2,4-dinitrobenzene (DFDNB), 1-ethyl-3-[3-dimethylaminopropyl]carbodiimide hydrochloride (EDC or EDAC), sulfosuccinimidyl-4-(N-maleimidomethyl)cyclohexane-1-carboxylate (sulfo-SMCC), N-hydroxysulfosuccinimide (sulfo-NHS), hydroxylamine and Sulfo-LC-SPDP (N-succinimidyl 3-(2-pyridyldithio)-propionate), or sulfosuccinimidyl 6-(3'-[2-pyridyldithio]-propionamido)hexanoate (sulfo-LC-SPDP). Magnetic beads, and the technology for coupling magnetic beads to an affinity agent, are known in the art. Magnetic beads are commercially available, e.g., Dynabeads™ magnetic beads (Life Technologies, Grand Island, N.Y.); PureProteome™ magnetic beads (EMD Millipore, Billerica, Mass.); and xMAP® Antibody Coupling Kit (Luminex Corporation, Austin, Tex.).

In some embodiments, a magnetic bead is linked to an affinity agent that forms part of an antigen-affinity agent-label complex, and the antigen-affinity agent-label complex is separated from uncomplexed components (i.e., components that are not bound in the antigen-affinity agent-label complex) using a magnet that attracts the magnetic bead linked to the affinity agent in the complex. In some embodiments, the magnetic separation is performed using a magnetic separation apparatus that comprises a magnet. For example, in some embodiments, the magnetic separation apparatus is a magnetic rack. Magnetic racks are commercially available, e.g., from Invitrogen.

In some embodiments, complexed antigen-affinity agent-label in the sample is separated from uncomplexed components (e.g., uncomplexed affinity agent(s) and uncomplexed antigen, if present, in the sample) by buoyancy or filtration. For example, in some embodiments, a magnetic bead is linked to an affinity agent that forms part of an antigen-affinity agent-label complex, and the antigen-affinity agent-label complex is separated from uncomplexed components based on decreased buoyancy of magnetic beads in the antigen-affinity agent-label complex as compared to uncomplexed components, or by filtering for magnetic beads.

In some embodiments, the methods further comprise, after the step of separating antigen-affinity agent-label complex from uncomplexed components, and before the step of partitioning the separated sample, resuspending at least the label (e.g., label in the antigen-affinity agent-label complex or label cleaved from the antigen-affinity agent-label complex) in a solution. A suitable solution for resuspending the antigen-affinity agent-label complex can be determined by a person skilled in the art. In some embodiments, the solution is an aqueous solution, e.g., an aqueous buffer or a PCR master mix such as Droplet PCR Supermix (Bio-Rad Laboratories, Inc., Hercules, Calif.).

In some embodiments, the methods further comprise, after the step of separating antigen-affinity agent-label complex from uncomplexed components, and before the step of partitioning the separated sample, washing at least the label (e.g., label in the antigen-affinity agent-label complex or label cleaved from the antigen-affinity agent-label complex) from uncomplexed components. In some embodiments, the washing step comprises washing at least the label from free affinity agent(s) and free antigen, if present. The selection of appropriate wash conditions, wash buffers, etc. will vary based upon conditions such as antigen, affinity agent, etc. and can be determined by a person skilled in the art. A wash process can be repeated for additional washes as necessary. In some embodiments, no intervening wash step is performed after separating the antigen-affinity agent-label complex from uncomplexed components in the sample and before partitioning at least the label from the separated sample.

Detectable Labels

In some embodiments, an affinity agent as described herein is linked to a detectable label. The label can be linked directly to the affinity agent (e.g., by a covalent bond) or the attachment can be indirect (e.g., using a chelator or linker molecule). The terms "label" and "detectable label" are used synonymously herein.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. Intercalating dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenylindole hydrochloride).

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag), and protein tags (e.g., GST-tag, MBP-tag, GFP-tag).

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectably labeled (e.g., a fluorescently labeled, biotinylated, or radiolabeled alkyne or azide moiety).

Nucleic Acid Labels

Figure 3:
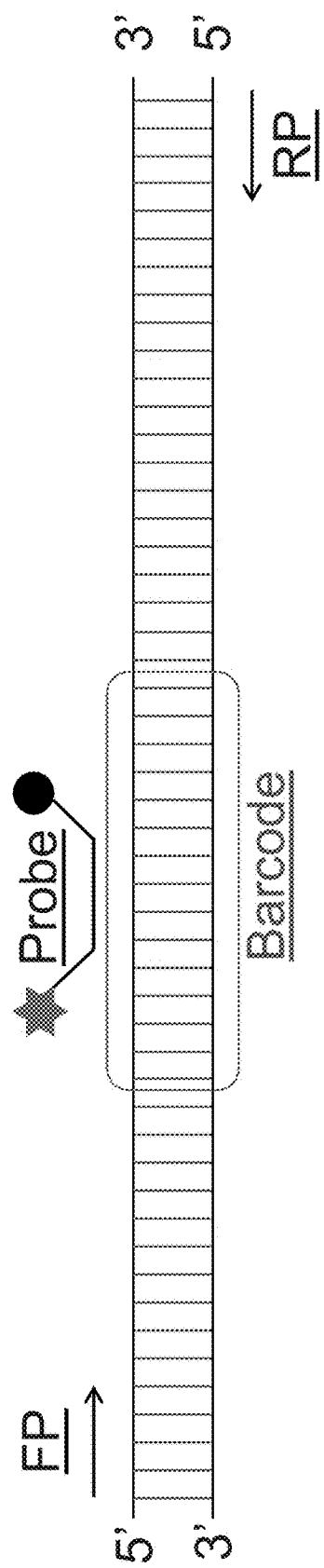
FIG. 3. Overview of tagged nucleic acids ("TNAs") for labeling an affinity agent. The nucleic acid can be barcoded specifically for a particular affinity agent (e.g., a specific secondary antibody). By making TNAs specific for particular affinity agents, a suite of TNAs can be constructed, each TNA having a specific signature sequence indicative of a specific affinity agent. The TNA barcode can be detected by nucleic acid amplification of the TNA in the presence of complementary primers and a probe having a fluorophore and a quencher.

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length. In some embodiments, the nucleic acid label comprises a detectable tag (e.g., a "tagged nucleic acid"). In some embodiments, the detectable tag is an optical agent (e.g., a fluorophore or intercalating dye) as described herein. In some embodiments, the detectable tag is a sequence that is complementary or substantially complementary to a detectable probe, e.g., a TaqMan® probe (Life Technologies, Grand Island, N.Y.) having a fluorophore and a quencher that anneals to the nucleic acid region, thereby enabling detection of the nucleic acid label. In some embodiments, the nucleic acid label is "barcoded" specifically for a particular affinity agent (i.e., has a specific recognition signature for a specific affinity agent). See FIG. 3.

As a non-limiting example, in some embodiments, the label is a nucleic acid label. In some embodiments, the nucleic acid label is covalently bound to an affinity agent (e.g., antibody) at a chemically suitable location.

Enzyme Labels

In some embodiments, the label is an enzyme, and the presence of the label (e.g., in an antigen-affinity agent-label complex) is detected by detecting a product generated by the enzyme. Examples of suitable enzymes include, but are not limited to, a polymerase (e.g., DNA polymerase), urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

As a non-limiting example, in some embodiments, the label is a DNA polymerase, and the detecting comprises detecting a nucleic acid amplification product that is generated by the DNA polymerase. See FIGS. 2A-B. In some embodiments, the DNA polymerase is a thermostable DNA polymerase, e.g., Taq polymerase. In some embodiments, the DNA polymerase is a chemical- or antibody-mediated hot start Taq polymerase. Taq polymerases and hot start Taq polymerases are readily commercially available (e.g., Fast-Start Taq DNA polymerase, available from Roche Applied Science, or iTaq™ DNA polymerase, available from Bio-Rad Laboratories, Inc.). One of skill will recognize that other DNA polymerases, such as other strains and/or mutations of Taq, can be used for detecting a nucleic acid amplification product.

Techniques for attaching detectable labels to affinity agents are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996). The techniques are also available as parts of commercially available kits (e.g., Thunder-Link® and Lightning-Link® from Innova Biosciences Ltd., Cambridge, United Kingdom). In some embodiments, a detectable label is attached to an affinity agent via a covalent bond, ionic bond, hydrogen bonding, or by Van der Waals interactions.

Detection

A detectable label (e.g., a label as described herein) can be detected using any of a variety of detector devices. Exemplary detection methods include radioactive detection, optical absorbance detection (e.g., fluorescence or chemiluminescence), or mass spectral detection. As a non-limiting example, a fluorescent label can be detected using a detector device equipped with a module to generate excitation light that can be absorbed by a fluorophore, as well as a module to detect light emitted by the fluorophore.

In some embodiments, detectable labels in partitioned samples can be detected in bulk. For example, partitioned samples (e.g., droplets) can be partitioned into one or more wells of a plate, such as a 96-well or 384-well plate, and the signal(s) (e.g., fluorescent signal(s)) may be detected using a plate reader.

In some embodiments, the detector further comprises handling capabilities for the partitioned samples (e.g., droplets), with individual partitioned samples entering the detector, undergoing detection, and then exiting the detector. In some embodiments, partitioned samples (e.g., droplets) may be detected serially while the partitioned samples are flowing. In some embodiments, partitioned samples (e.g., droplets) are arrayed on a surface and a detector moves relative to the surface, detecting signal(s) at each position containing a single partition. Examples of detectors are provided in WO 2010/036352, the contents of which are incorporated herein by reference. In some embodiments, detectable labels in partitioned samples can be detected serially without flowing the partitioned samples (e.g., using a chamber slide).

Following acquisition of fluorescence detection data, a general purpose computer system (referred to herein as a "host computer") can be used to store and process the data. A computer-executable logic can be employed to perform such functions as subtraction of background signal, assignment of target and/or reference sequences, and qualification and/or quantification of the data. A host computer can be useful for displaying, storing, retrieving, or calculating diagnostic results from the molecular profiling; storing, retrieving, or calculating raw data from expression analysis; or displaying, storing, retrieving, or calculating any sample or patient information useful in the methods of the present invention.

The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

Partitioning Samples for Detection

The separated sample comprising at least the label to be detected (e.g., in the antigen-affinity agent-label complex or cleaved from the antigen-affinity agent-label complex) is partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are microchannels. Methods and compositions for partitioning a sample are described, for example, in published patent applications WO 2010/036352, US 2010/0173394, US 2011/0092373, and US 2011/0092376, the entire content of each of which is incorporated by reference herein.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous solution comprising the label(s) to be detected. In some embodiments, the aqueous sample comprising the label(s) to be detected comprises a buffered solution and reagents for detecting the label(s). The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing.

Following conversion, the microcapsules may be stored at about −70°, −20°, 0°, 3°, 4°, 5°, 6°, 7°, 8°, 9°, 10°, 15°, 20°, 25°, 30°, 35°, or 40° C. In some embodiments, these capsules are useful in biomedical applications, such as stable, digitized encapsulation of macromolecules, particularly aqueous biological fluids comprising a mix of target molecules such as nucleic acids, proteins, or both together; drug and vaccine delivery; biomolecular libraries; clinical imaging applications; and others.

The microcapsule partitions may contain one or more affinity agents as described herein and may resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions may be incubated per mL. In some embodiments, the sample-probe incubations occur in a single well, e.g., a well of a microtiter plate, without inter-mixing between partitions. The microcapsules may also contain other components necessary for the incubation.

In some embodiments, the sample is partitioned into at least 500 partitions (e.g., droplets), at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that at least a majority of partitions have no more than 1, 2, 3, 4, 5, 6, 7, 8, 9, 10, 15, 20, 30, 40, 50, 60, 70, 80, 90, 100, 200, 300, 400, or 500 copies of a label. In some embodiments, a majority of the partitions have no more than 1, 2, 3, 4, 5, 6, 7, 8, 9, 10, 15, 20, 30, 40, 50, 60, 70, 80, 90, 100, 200, 300, 400, or 500 copies of the one or more labels to be detected. In some embodiments, on average no more than 1, 2, 3, 4, 5, 6, 7, 8, 9, 10, 15, 20, 30, 40, 50, 60, 70, 80, 90, 100, 200, 300, 400, or 500 copies of the one or more labels are present per partition.

In some embodiments, the sample is partitioned into a sufficient number of partitions such that, on average, at least one partition lacks a copy of the label. In some embodiments, the sample is partitioned into a sufficient number of partitions such that, on average, at least 5, 10, 15, 20, 25, 30, 35, 40, 50, 60, 70, 80, 90, 100, 125, 150, 175, 200, 250, 300, 350, 400, 450, or 500 partitions lack a copy of the label. In some embodiments, the sample is partitioned into a sufficient number of partitions such that, on average, at least 5, 10, 15, 20, 25, 30, 35, 40, 50, 60, 70, 80, 90, 100, 125, 150, 175, 200, 250, 300, 350, 400, 450, or 500 partitions lack a copy of the label and such that, on average, at least 5, 10, 15, 20, 25, 30, 35, 40, 50, 60, 70, 80, 90, 100, 125, 150, 175, 200, 250, 300, 350, 400, 450, or 500 partitions have at least one copy of the label.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Digital Analysis

A digital readout assay, e.g., digital analysis, can be used to detect and quantify one or more antigens in a sample by partitioning at least the labels from the separated sample (e.g., labels in antigen-affinity agent-label complexes or labels cleaved from antigen-affinity agent-label complexes) and identifying the partitions containing the label. Generally, the process of digital analysis involves determining for each partition of a sample whether the partition is positive or negative for the presence of the label or labels to be detected. If the antigen-affinity agent-label complex comprises antigen and label that are at an unknown ratio, then the presence of label corresponds to a positive detection of the antigen. If the antigen-affinity agent-label complex comprises antigen and label at a known ratio (i.e., 1:1 ratio), the amount of label that is detected for a sample can be correlated to the amount of antigen present in the sample. For quantifying the amount of antigen in a sample (e.g., quantifying the concentration or number of copies of an antigen in a sample), the partitions are examined for the presence or absence of a detectable signal in each partition. A partition is "positive" for the presence of the antigen if a signal is detected in the partition. In some embodiments, the signal that is detected in the partition is generated by a label linked to an affinity agent in an antigen-affinity agent-label complex (e.g., a fluorescent, chemiluminescent, radioactive, or enzymatic label linked to the affinity agent). A partition is "negative" for the presence of the antigen if no signal detected in the partition.

In some embodiments, a detector that is capable of detecting a signal or multiple signals is used to analyze each partition for the presence or absence of the antigen. For example, in some embodiments a two-color reader (fluorescence detector) is used. The fraction of positive-counted partitions can enable the determination of absolute concentrations for the antigen or antigens to be measured.

Once a binary "yes-no" result has been determined for each of the partitions of the sample, the data for the partitions is analyzed using an algorithm based on Poisson statistics to quantify the amount of antigen in the sample. Statistical methods for quantifying the concentration or amount of an antigen or antigens is described, for example, in WO 2010/036352, which is incorporated by reference herein in its entirety.

Amplification of Nucleic Acid

In some embodiments, the methods described herein comprise an amplification step. In some embodiments, a nucleic acid label attached to an affinity agent as part of an antigen-affinity agent-label complex is amplified prior to the step of detecting a detectable signal from the label. For example, in some embodiments, the nucleic acid label is amplified in the presence of primers and a probe that specifically bind the nucleic acid label, and the probe generates a detectable (e.g., fluorescent) signal when the nucleic acid is amplified, thereby indicating the presence of an antigen-affinity agent-label complex.

In some embodiments, for example when a label attached to an affinity agent is a DNA polymerase, the amplification step comprises contacting the sample comprising the labeled affinity agent with a nucleic acid and detecting a nucleic acid amplification product generated by the label (e.g., the DNA polymerase). In some embodiments, the nucleic acid to be amplified comprises a sequence that is complementary or substantially complementary to a probe that generates a detectable (e.g., fluorescent) signal when the nucleic acid is amplified, thereby indicating the presence of an antigen-affinity agent-label complex.

As a non-limiting example, a system such as the TaqMan® system can be used. This system utilizes a short oligonucleotide probe (e.g., about 20-25 bases in length) that is labeled with two different fluorescent dyes. In some embodiments, the 5' terminus of the probe is attached to a reporter dye, or "fluorescer," and the 3' terminus is attached to a quenching moiety, or "quencher." In some embodiments, the dyes are attached at other locations on the probe. The probe can be designed to have at least substantial sequence complementarity with the probe-binding site on the nucleic acid to be amplified. Upstream and downstream PCR primers that bind to regions that flank the probe binding site are utilized for amplifying the nucleic acid.

When the fluorogenic probe is intact, energy transfer between the fluorescer and quencher moiety occurs and quenches emission from the fluorescer. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorescer and quencher moieties. This results in an increase of reporter emission intensity that can be measured by an appropriate detector. Detection and/or quantification of the antigen is determined by mathematical conversion of fluorescent signal to number of antigens according to methods known in the art. Additional details regarding fluorogenic methods for detecting PCR products are described, for example, in U.S. Pat. No. 5,210,015 to Gelfand, U.S. Pat. No. 5,538,848 to Livak, et al, and U.S. Pat. No. 5,863,736 to Haaland, each of which is incorporated by reference in its entirety, as well as Heid, C. A., et al., Genome Research, 6:986-994 (1996); Gibson, U. E. M, et al., Genome Research 6:995-1001 (1996); Holland, P. M., et al, Proc. Natl. Acad. Sci. USA 4 88:7276-7280, (1991); and Livak, K. J., et al., PCR Methods and Applications 357-362 (1995).

As another non-limiting example, structured probes (e.g., "molecular beacons") can be utilized to detect a nucleic acid amplification product. With molecular beacons, a change in conformation of a probe as it hybridizes to a complementary region of the amplified product results in the formation of a detectable signal. In addition to the target-specific portion, the probe includes additional sections, generally one section at the 5' end and another section at the 3' end, that are complementary to each other. One end section is typically attached to a reporter dye and the other end section is usually attached to a quencher dye. In solution, the two end sections can hybridize with each other to form a stem-loop structure.

In this conformation, the reporter dye and quencher are in sufficiently close proximity that fluorescence from the reporter dye is effectively quenched by the quencher. The hybridized probe, in contrast, has a linearized conformation which decreases the extent of quenching. Thus, by monitoring emission changes for the reporter dye, it is possible to indirectly monitor the formation of amplification product. Probes of this type and methods of their use is described further, for example, by Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998).

In some embodiments, the method comprises incubating the sample comprising the labeled affinity agent with the nucleic acid under conditions suitable for amplifying the nucleic acid. For example, the sample can be incubated with amplification reagents (dNTPs, primers, probes, blocking agents, biopreservatives, etc.). Suitable conditions for amplifying the nucleic acid will depend, e.g., on the nature of the DNA polymerase and the nucleic acid to be amplified, and can be readily determined by a person of skill in the art.

In some embodiments, following the separation of the antigen-affinity agent-label complex, the label from the separated sample (e.g., label in an antigen-affinity agent-label complex or label cleaved from antigen-affinity agent-label complex) is resuspended in a solution (e.g., an aqueous buffer) comprising reagents for amplification (e.g., dNTPs, primers, TaqMan® probe, etc.). In some embodiments, the solution is partitioned into a plurality of partitions before the amplification step. In some embodiments, amplification is performed before the partitioning step.

Methods for nucleic acid amplification are well known in the art and include, but are not limited to, polymerase chain reaction (PCR), quantitative PCR, real time PCR, hot start PCR, single cell PCR, nested PCR, in situ colony PCR, digital PCR, Droplet Digital™ PCR (ddPCR), emulsion PCR, ligase chain reaction (LCR), transcription based amplification system (TAS), nucleic acid sequence-based amplification (NASBA), strand displacement amplification (SDA), rolling circle amplification (RCA), and hyperbranched RCA (HRCA).

In some embodiments, the amplification is performed using Droplet Digital™ PCR (ddPCR). Devices for performing ddPCR are known in the art. For example, ddPCR can be performed with the QX100™ Droplet Digital™ PCR System (Bio-Rad Laboratories, Inc., Hercules, Calif.). Methods and devices for performing ddPCR are also described, for example, in WO 2010/036352 and WO 2012/129187, each of which is incorporated by reference herein.

III. Methods of Detecting an Antibody Analyte

In another aspect, methods of detecting an antibody analyte of interest in a sample are provided, wherein the antibody analyte specifically binds to a particular antigen. In some embodiments, the method comprises:

contacting the sample with the antigen and a first affinity agent, wherein the first affinity agent is linked to a magnetic bead and specifically binds to the antigen, thereby forming an analyte-antigen-affinity agent complex;

contacting the sample comprising the analyte-antigen-affinity agent complex with a second affinity agent, wherein the second affinity agent comprises a label and specifically binds to the antibody analyte, thereby forming an analyte-antigen-affinity agent-label complex;

separating the analyte-antigen-affinity agent-label complex from uncomplexed components in the sample based on the presence or absence of the magnetic bead, thereby generating a separated sample comprising the analyte-antigen-affinity agent-label complex;

partitioning at least the label from the separated sample into a plurality of partitions; and detecting the presence of the label in at least one partition; thereby detecting the presence of the antibody analyte.

In some embodiments, the label that is partitioned is in the analyte-antigen-affinity agent-label complex. In some embodiments, the label is cleaved from the analyte-antigen-affinity agent-label complex prior to the partitioning step.

The methods described herein can be used to detect one or more antibody analytes in any type of sample (e.g., biological sample). In some embodiments, two, three, four, five, or more different antibody analytes are to be detected. In some embodiments, wherein two or more different antibody analytes are to be detected, the two or more different antibody analytes specifically bind to the same antigen. In some embodiments, wherein two or more different antigens are to be detected, the two or more different antibody analytes specifically bind to different antigens.

For detecting an antibody analyte, the reagents (e.g., affinity agents, detectable labels, and magnetic beads) and conditions (e.g., detection, partitioning, and digital analysis) for carrying out the methods can be any of the reagents and/or conditions described herein, e.g., in Section II above.

IV. Partition Libraries

In another aspect, partition libraries comprising a plurality of partitions for carrying out the methods as described herein are provided. In some embodiments, the partition library comprises a plurality of partitions for detecting the presence of an antigen in a sample. In some embodiments, the partition library comprises two or more partitions, wherein at least some partitions of the library (e.g., at least 5%, 10%, 15%, 20%, 25%, 30%, 35%, 40%, 45%, 50%, 55%, 60%, 65%, 70%, 75%, 80%, 85%, 90%, or 95% of the partitions in the library) comprise one, two, three, four, five or more different affinity agents. In some embodiments, at least some of the partitions comprise a first affinity agent and a second affinity agent; wherein the first affinity agent comprises a label; wherein the second affinity agent is linked to a magnetic bead; and wherein each of the first and second affinity agents specifically binds to the antigen, if present. In some embodiments, at least some of the partitions comprise a first affinity agent, a second affinity agent, and a third affinity agent, wherein each of the first and second affinity agents specifically binds to an antigen, if present, wherein the second affinity agent is linked to a magnetic bead, and wherein the third affinity agent comprises a label and specifically binds to the first affinity agent.

In some embodiments, the partition library comprises a plurality of partitions for detecting the presence of an antibody analyte in a sample, wherein the antibody analyte specifically binds to a particular antigen. In some embodiments, at least some of the partitions comprise the antigen, a first affinity agent, and a second affinity agent; wherein the first affinity agent is linked to a magnetic bead and specifically binds to the antigen; and wherein the second affinity agent comprises a label and specifically binds to the antibody analyte, if present.

In some embodiments, the partition library comprises at least 500, 1000, 2000, 3000, 4000, 5000, 6000, 7000, 8000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 10,000,000, 20,000,000, 30,000,000, 40,000,000, 50,000,000, 60,000,000, 70,000,000, 80,000,000, 90,000,000, 100,000,000, 150,000,000, or 200,000,000 partitions.

The affinity agent for the partitions of the partition library can be any affinity agent described herein. In some embodiments, the affinity agent(s) is an antibody. In some embodiments, the affinity agent(s) is an antibody fragment. In some embodiments, the affinity agent(s) is a non-antibody protein scaffold. In some embodiments, the affinity agent(s) is an antibody mimetic. In some embodiments, the affinity agent(s) is an aptamer. In some embodiments, an affinity agent is labeled as described herein, e.g., with a nucleic acid label, an enzyme label, or a fluorophore label.

In some embodiments, at least some partitions of the partition library comprise one or more labels. In some embodiments, at least some partitions comprise two, three, four, five, or more different labels. In some embodiments, the sample is partitioned into a sufficient number of partitions such that, on average, at least 1, 5, 10, 15, 20, 25, 30, 35, 40, 50, 60, 70, 80, 90, 100, 125, 150, 175, 200, 250, 300, 350, 400, 450, or 500 partitions lack a copy of the label. In some embodiments, the sample is partitioned into a sufficient number of partitions such that, on average, at least 1, 5, 10, 15, 20, 25, 30, 35, 40, 50, 60, 70, 80, 90, 100, 125, 150, 175, 200, 250, 300, 350, 400, 450, or 500 partitions lack a copy of the label and such that, on average, at least 1, 5, 10, 15, 20, 25, 30, 35, 40, 50, 60, 70, 80, 90, 100, 125, 150, 175, 200, 250, 300, 350, 400, 450, or 500 partitions have at least one copy of the label.

In some embodiments, the partition library comprises a plurality of partitions that are solid partitions (e.g., wells or tubes). In some embodiments, the partitions are microchannels. In some embodiments, the partition library comprises a plurality of partitions that are fluid partitions (e.g., aqueous droplets within an oil phase). In some embodiments, the partitions are droplets. In some embodiments, the partitions are microcapsules. Examples of suitable partitions and methods of generating partitions are described above.

In some embodiments, the partition library comprises partitions that are substantially uniform in shape and/or size. For example, in some embodiments, the partitions (e.g., droplets) are substantially uniform in average diameter. In some embodiments, the partitions (e.g., droplets) have an average diameter of about 0.001, 0.005, 0.01, 0.05, 0.1, 0.5, 1, 5, 10, 20, 30, 40, 50, 60, 70, 80, 90, 100, 150, 200, 300, 400, 500, 600, 700, 800, 900, or 1000 microns. In some embodiments, the partitions (e.g., droplets) have an average diameter of less than about 1000, 900, 800, 700, 600, 500, 400, 300, 200, 100, 50, or 25 microns. In some embodiments, the partition library comprises partitions (e.g., droplets) that are non-uniform in shape and/or size.

In some embodiments, the partitions (e.g., droplets) are substantially uniform in volume. For example, in some embodiments, the partitions (e.g., droplets) have an average volume of about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, or 50 nL.

In some embodiments, the partitions (e.g., droplets) are stable and are capable of long-term storage. In some embodiments, the partitions can be stored at about −70°, −20°, 0°, 3°, 4°, 5°, 6°, 7°, 8°, 9°, 10°, 15°, 20°, 25°, 30°, 35°, or 40° C. for an extended period of time (e.g., for at least 30 days, at least 60 days, at least 90 days, or longer).

V. Kits

In another aspect, kits for detecting an antigen or for detecting an antibody analyte that specifically binds to an antigen according to the methods described herein are provided. In some embodiments, a kit comprises one or more affinity agents as described herein, e.g., one or more antibodies, antibody fragments, non-antibody protein scaffolds, antibody mimetics, and/or aptamers as described herein. In some embodiments, a kit further comprises one or more reagents for forming partitions, detection reagents, and/or reagents for nucleic acid amplification (e.g., buffers, enzymes, dNTPs, primers, TaqMan® probes, blocking agents, biopreservatives, and the like). In some embodiments, a kit for detecting an antibody analyte further comprises an antigen to which the antibody analyte specifically binds. In some embodiments, a kit further comprises instructions for carrying out the methods described herein.

VI. Examples

The following examples are offered to illustrate, but not to limit the claimed invention.

Example 1: Scheme 1 for Detecting an Antigen

This example demonstrates detecting an antigen of interest using two primary affinity agents (e.g., antibodies), each of which specifically binds to the antigen. A sample is contacted with primary antibody A and primary antibody B. Antibody B has a magnetic bead covalently attached. Following incubation with antibodies A and B, the sample is contacted with a secondary antibody C that is labeled with a tagged nucleic acid ("TNA"). The antigen-primary antibody-secondary antibody-TNA complex is purified from free primary antibody A and secondary antibody C by magnetic separation with washing, then the purified complex is resuspended and captured in droplets. Droplet digital PCR is performed to detect the presence of the TNA label and/or quantify the amount of TNA label in each droplet. Detection and/or quantification of the antigen is then determined by mathematical conversion of the signal from the label to the number of antigens. See FIG. 1.

Example 2: Scheme 2 for Detecting an Antigen

Figure 2A:
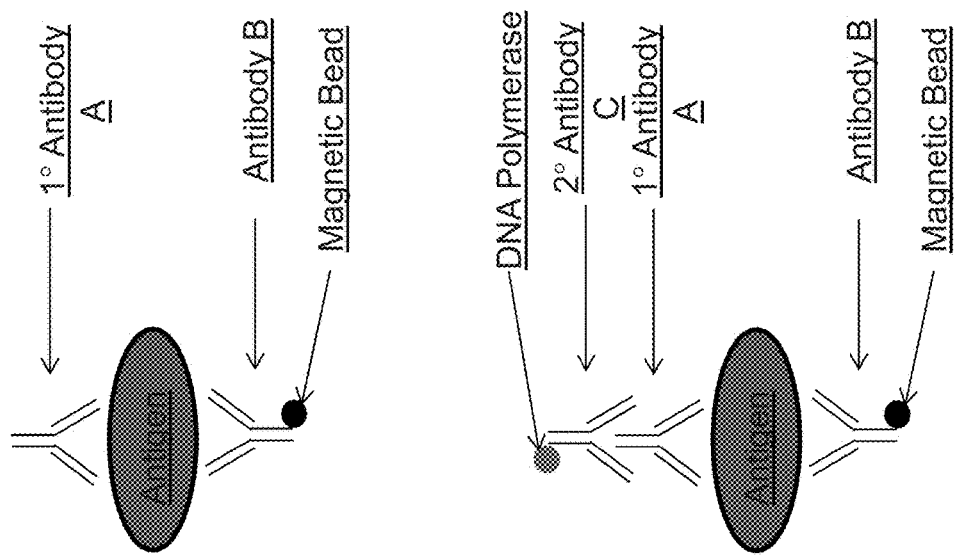
FIG. 2A-B. Overview of an ELISA-like variant scheme ("Scheme 2") for detecting an antigen. (A) According to this scheme, an antigen binds specifically to two affinity agents (primary antibodies), A and B. Antibody B has a magnetic bead covalently attached. The antigen-antibody complex is contacted with a secondary antibody C that is coupled to a DNA polymerase such as Taq, Fast Start Taq, or some other polymerase (e.g., a mutagenized or variant DNA polymerase with desired properties for the application). (B) The antigen-primary antibody-secondary antibody-DNA polymerase complex is purified from free primary antibody A and secondary antibody C by magnetic separation, then the complex is resuspended in a master mix suitable for digital droplet formation and PCR amplification (e.g., including a nucleic acid suitable for amplification, dNTPs, appropriate forward and reverse primers, and TaqMan® probe). The resuspended complex is captured in droplets, then amplification of a nucleic acid and detection of a fluorogenic signal from the TaqMan® probe is performed to detect the antigen.
Figure 2B:
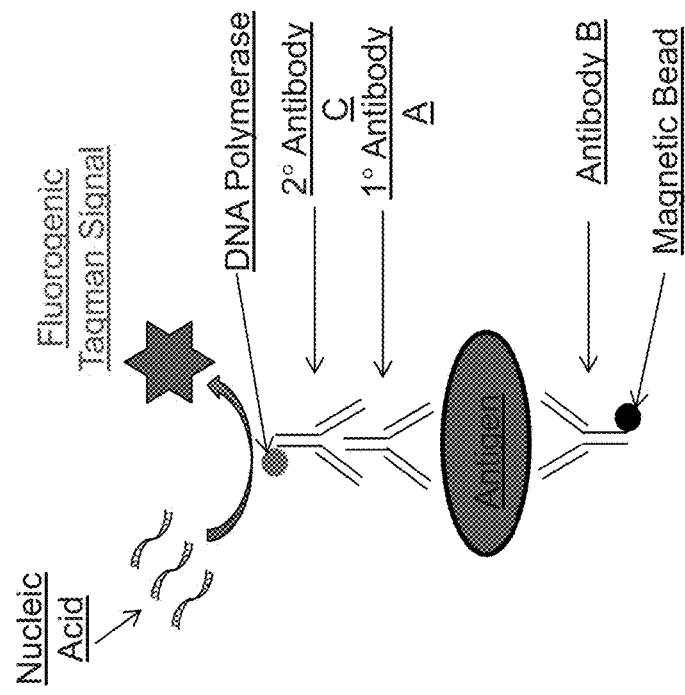

This example demonstrates detecting an antigen using two primary affinity agents (e.g., antibodies), each of which specifically binds to the antigen. In this scheme, an enzyme-linked secondary antibody is added that converts a substrate into a detectable form for detecting the presence of the antigen. A sample is contacted with primary antibody A and primary antibody B. Antibody B has a magnetic bead covalently attached. Following incubation with antibodies A and B, the sample is contacted with a secondary antibody C that binds specifically to antibody A. The secondary antibody C is coupled to a DNA polymerase such as Taq, Fast Start Taq, or some other polymerase (e.g., a mutagenized or variant DNA polymerase with desired properties for the application) or to another enzyme (FIG. 2A). The antigen-primary antibody-secondary antibody-DNA polymerase complex is purified from free primary and secondary antibodies by magnetic separation with washing, then the complex is resuspended in a master mix or appropriate buffer suitable for digital droplet formation and PCR amplification or other means of fluorogenic or chromogenic detection (e.g., including nucleic acid(s) suitable for amplification, appropriate forward and reverse primers, and TaqMan® probe; or an appropriate substrate for the enzyme coupled to the secondary antibody C and reagents for fluorogenic or chromogenic detection). The resuspended complex is captured in droplets, then the nucleic acid is amplified and the fluorogenic signal that is generated from the TaqMan® probe is detected and/or quantified, or the fluorogenic or chromogenic signal generated by the enzyme is detected and/or quantified (FIG. 2B). Detection and/or quantification of the antigen is then determined by mathematical conversion of the signal from the TaqMan® probe to the number of antigens.

Example 3: Scheme 3 for Detecting an Antigen

Figure 4:
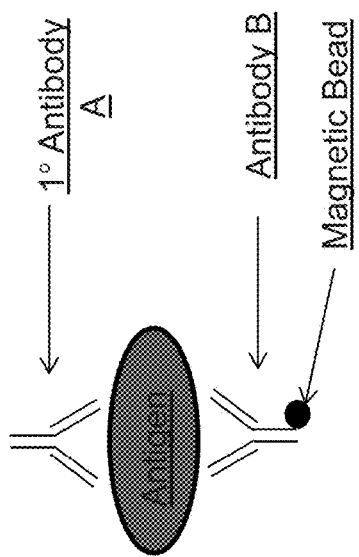
FIG. 4. Overview of a detection scheme using a fluorophore as a label ("Scheme 3"). According to this scheme, an antigen binds specifically to two affinity agents (primary antibodies), A and B. Antibody B has a magnetic bead covalently attached. The antigen-antibody complex is contacted with a secondary antibody C that is labeled with a fluorescent label (e.g., fluorophore). Free primary antibody A and secondary antibody C are washed away by magnetic separation, then the antigen-primary antibody-secondary antibody-fluorophore complex is captured in droplets. The antigen is detected by detecting the fluorescent signal generated by the fluorescent label.
Figure 4:
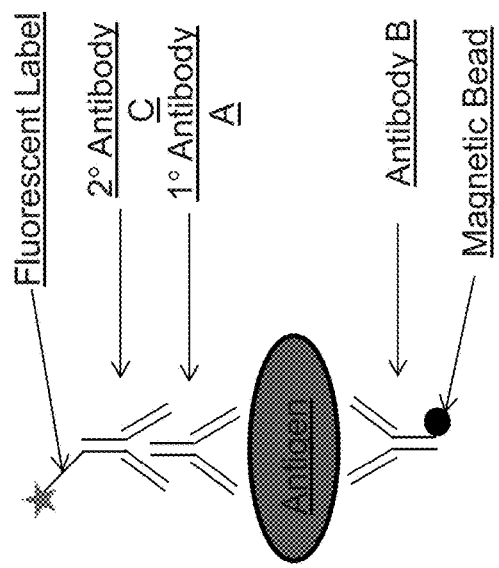

This example demonstrates detecting an antigen of interest using two primary affinity agents (e.g., antibodies), each of which specifically binds to the antigen. A sample is contacted with primary antibody A and primary antibody B. Antibody B has a magnetic bead covalently attached. Following incubation with antibodies A and B, the sample is contacted with a secondary antibody C that is labeled with a fluorophore. The antigen-primary antibody-secondary antibody-fluorophore complex is purified from free primary antibody A and secondary antibody C by magnetic separation with washing, then the purified complex is resuspended and captured in droplets. The fluorescent signal generated by the fluorophore label is detected according to any method described herein. Detection and/or quantification of the antigen is then determined by mathematical conversion of the signal from the label to the number of antigens. See FIG. 4.

Example 4: Scheme for Detecting an Antibody Analyte

Figure 5:
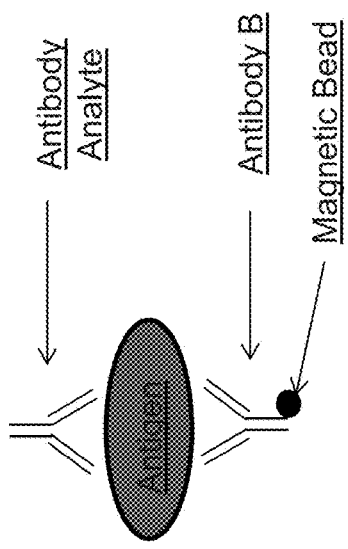
FIG. 5. Overview of a detection scheme for detecting an antibody analyte of interest that binds to an antigen ("Scheme 4"). According to this scheme, an antibody analyte of interest binds specifically to an antigen. An affinity agent (primary antibody B) covalently attached a magnetic bead also specifically binds to the antigen. The analyte-antigen-antibody complex is contacted with a labeled secondary antibody C. The label on secondary antibody C can be a label as described herein, e.g., a fluorophore (depicted in FIG. 5), a TNA, or a DNA polymerase or other enzyme capable of converting a substrate to a detectable signal. The free antigen and secondary antibody C are washed by magnetic separation, then the antigen-antibody-label complex is captured in droplets. The antibody analyte is detected as described herein, e.g., by detecting the fluorescent signal generated by the fluorescent label.
Figure 5:
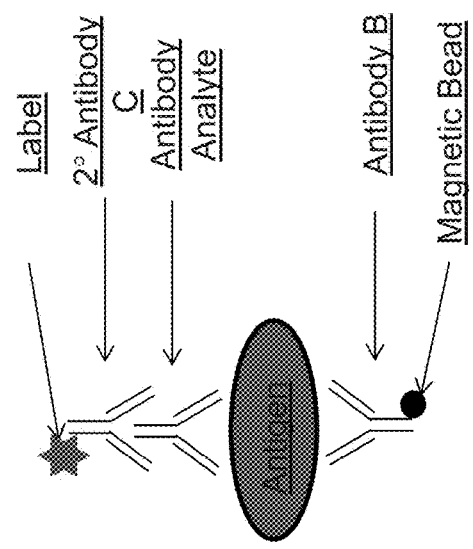

This example demonstrates detecting an antibody analyte of interest that binds to a particular antigen. A sample comprising an antibody analyte of interest is contacted with an antigen to which the antibody analyte specifically binds and an affinity agent (e.g., a primary antibody B) that also specifically binds to the antigen. The affinity agent has a magnetic bead covalently attached. Following incubation with the antigen and the affinity agent (e.g., primary antibody B), the sample is contacted with a labeled affinity agent (e.g., a secondary antibody C). The label can be any label described herein, for example but not limited to a tagged nucleic acid (TNA), a DNA polymerase or other enzyme capable of converting a substrate to a detectable signal, or a fluorescent label. The analyte-antigen-antibody-label complex is purified from free antigen and affinity agent by magnetic separation with washing, then the purified complex is resuspended and captured in droplets. The label is then detected as described herein. For example, if the label is a TNA label, droplet digital PCR is performed to detect the presence of the TNA label and/or quantify the amount of TNA label in each droplet. If the label is a fluorophore, the fluorescent signal generated by the fluorophore is detected. Detection and/or quantification of the antibody analyte is then determined by mathematical conversion of the signal from the label to the number of analytes. See FIG. 5.

Example 5: Two-Antibody Scheme for Detecting an Antigen

Figure 6:
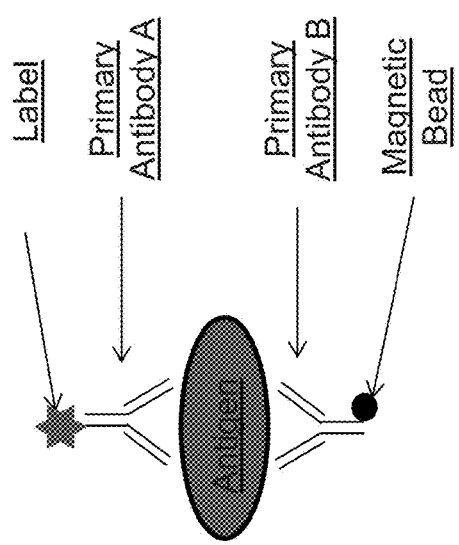
FIG. 6. Overview of a two-antibody detection scheme for detecting an antigen ("Scheme 5"). According to this scheme, an antigen binds specifically to two affinity agents (primary antibodies), A and B. Antibody A is labeled (e.g., with a tagged nucleic acid or a fluorescent label), and antibody B is attached to a magnetic bead. Free primary antibody A is washed from the label-primary antibody-antigen complex by magnetic separation, then the antigen-primary antibody-antigen complex is captured in droplets. The antigen is detected by detecting the presence of the label, e.g., a fluorescent label (e.g., flurophore) that is detected by detecting the fluorescent signal generated by the fluorescent label, or a TNA label that is amplified by ddPCR.

This example demonstrates detecting an antigen of interest using two primary affinity agents (e.g., antibodies), each of which specifically binds to the antigen. A sample is contacted with primary antibody A and primary antibody B. Antibody A is labeled, e.g., with a tagged nucleic acid or a fluorescent label, e.g., fluorophore. Antibody B has a magnetic bead covalently attached. Following incubation with antibodies A and B, the antigen-primary antibody-secondary antibody-fluorophore complex is purified from free primary antibody A by magnetic separation with washing, then the purified complex is resuspended and captured in droplets. The presence or absence of the label is then detected for each droplet (e.g., a fluorescent signal generated by the fluorophore label can be detected according to any detection method described herein, or droplet digital PCR is performed to detect the presence of a TNA label and/or quantify the amount of TNA label in each droplet). Detection and/or quantification of the antigen is then determined by mathematical conversion of the amount of/signal from the label to the number of antigens. See FIG. 6.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting an antigen in a sample, the method comprising:
   contacting the sample with a first affinity agent and a second affinity agent, wherein the second affinity agent is linked to a magnetic bead and wherein the first and second affinity agents specifically bind to the antigen, if present;
   contacting the sample comprising the first and second affinity agents with a third affinity agent, wherein the third affinity agent comprises a label and wherein the third affinity agent specifically binds to the first affinity agent, thereby forming an antigen-affinity agent-label complex;
   separating the antigen-affinity agent-label complex from uncomplexed components in the sample comprising the antigen-affinity agent-label complex based on the presence or absence of the magnetic bead, thereby generating a separated sample comprising the antigen-affinity agent-label complex;
   partitioning at least the label from the separated sample into a plurality of partitions; and
   detecting the presence of the label in at least one partition; thereby detecting the presence of the antigen.

2. A method of detecting an antigen in a sample, the method comprising:
   contacting the sample with a first affinity agent and a second affinity agent, wherein the first affinity agent comprises a label, wherein the second affinity agent is linked to a magnetic bead, and wherein the first and second affinity agents specifically bind to the antigen, if present, thereby forming an antigen-affinity agent-label complex;
   separating the antigen-affinity agent-label complex from uncomplexed components in the sample comprising the antigen-affinity agent-label complex based on the presence or absence of the magnetic bead, thereby generating a separated sample comprising the antigen-affinity agent-label complex;
   partitioning at least the label from the separated sample into a plurality of partitions; and detecting the presence of the label in at least one partition; thereby detecting the presence of the antigen.

3. The method of claim 1, wherein the label that is partitioned is in the antigen-affinity agent-label complex.

4. The method of claim 1, wherein the label is cleaved from the antigen-affinity agent-label complex prior to the partitioning step.

5. The method of claim 1, wherein the label is a nucleic acid label.

6. The method of claim 5, wherein the nucleic acid label is amplified prior to the detecting step.

7. The method of claim 1, wherein the label is an enzyme, and the detecting comprises detecting a product generated by the enzyme.

8. The method of claim 1, wherein the label is a fluorophore.

9. The method of claim 1, wherein the antigen-affinity agent-label complex is separated from uncomplexed components in the sample comprising the antigen-affinity agent-label complex using a magnet that attracts the magnetic bead linked to the second affinity agent in the antigen-affinity agent-label complex.

10. A method of detecting in a sample an antibody analyte that specifically binds to an antigen, the method comprising:
    contacting the sample with the antigen and a first affinity agent, wherein the first affinity agent is linked to a magnetic bead and specifically binds to the antigen, thereby forming an analyte-antigen-affinity agent complex;
    contacting the sample comprising the analyte-antigen-affinity agent complex with a second affinity agent, wherein the second affinity agent comprises a label and specifically binds to the antibody analyte, thereby forming an analyte-antigen-affinity agent-label complex;
    separating the analyte-antigen-affinity agent-label complex from uncomplexed components in the sample based on the presence or absence of the magnetic bead, thereby generating a separated sample comprising the analyte-antigen-affinity agent-label complex;
    partitioning at least the label from the separated sample into a plurality of partitions; and
    detecting the presence of the label in at least one partition; thereby detecting the presence of the antibody analyte.

11. The method of claim 10, wherein the label that is partitioned is in the analyte-antigen-affinity agent-label complex.

12. The method of claim 10, wherein the label is cleaved from the analyte-antigen-affinity agent-label complex prior to the partitioning step.

13. The method of claim 10, wherein the label is a nucleic acid label.

14. The method of claim 13, wherein the nucleic acid label is amplified prior to the detecting step.

15. The method of claim 10, wherein the label is an enzyme, and the detecting comprises detecting a product generated by the enzyme.

16. The method of claim 10, wherein the label is a fluorophore.

17. The method of claim 10, wherein the analyte-antigen-affinity agent-label complex is separated from uncomplexed components in the sample comprising the analyte-antigen-affinity agent-label complex using a magnet that attracts the magnetic bead linked to the first affinity agent in the analyte-antigen-affinity agent-label complex.

\* \* \* \* \*